United States Patent [19]
Schneider

[11] Patent Number: 5,312,916
[45] Date of Patent: May 17, 1994

[54] PROCESS FOR PREPARING 3-AMINO-9,13B-DIHYDRO-1H-DIBENZ(C,F)IMIDAZO(1,5-A)AZEPINE-HYDROCHLORIDE

[75] Inventor: Heinrich Schneider, Ingelheim am Rhein, Fed. Rep. of Germany

[73] Assignee: Boehringer Ingelheim KG, Ingelheim am Rhein, Fed. Rep. of Germany

[21] Appl. No.: 824,415

[22] Filed: Jan. 23, 1992

[30] Foreign Application Priority Data

Jan. 25, 1991 [DE] Fed. Rep. of Germany ....... 4102148

[51] Int. Cl.$^5$ ........................................... C07D 487/04
[52] U.S. Cl. ........................................... 540/579
[58] Field of Search ........................................... 540/579

[56] References Cited

U.S. PATENT DOCUMENTS 4,313,931 2/1982 Walther et al. .................... 540/579

OTHER PUBLICATIONS

March, *Advanced Organic Chem.*, 3rd ed (1985), John Wiley and Sons, pp. 378, 691–692.
Finar, *Chemistry*, vol. I, (1973), Longman Group, p. 623.
Wolfe and Hasan, Canadian Journal of Chem., 48, pp. 3572–3579, (1970).
Buschauer, Arch. Pharm. (Weinheim), 320, pp. 377–378 (1987).

*Primary Examiner*—Mukund J. Shah
*Assistant Examiner*—Philip Datlow
*Attorney, Agent, or Firm*—D. E. Frankhouser; A. R. Stempel; M-E. M. Timbers

[57] ABSTRACT

The present invention relates to a process for preparing 3-amino-9,13b-dihydro-1H-dibenz[c,f]-imidazo[1,5-a]azepine-hydrochloride, as follows:

a) hydrogenating 6-phthalimidomethyl-5H-dibenz[b,e]-azepine, to produce 6-(phthalimidomethyl)-6,11-dihydro-5H-dibenz[b,e]azepine;

b) reacting the 6-(phthalimidomethyl)-6,11-dihydro-5H-dibenz[b,e]azepine with hydrazine, to produce 6-aminomethyl-6,11-dihydro-5H-dibenz[b,e]azepine;

c) reacting the 6-aminomethyl-6,11-dihydro-5H-dibenz[b,e]azepine with bromocyanogen, to produce 3-amino-9,13b-dihydro-1H-dibenz[c,f]imidazo[1,5-a]azepine; and d) precipitating the 3-amino-9,13b-dihydro-1H-dibenz[c,f]imidazo[1,5-a]azepine in the presence of DMF and HCl, to produce 3-amino-9,13b-dihydro-1H-dibenz[c,f]imidazo[1,5-a]azepine-hydrochloride.

7 Claims, No Drawings

PROCESS FOR PREPARING 3-AMINO-9,13B-DIHYDRO-1H-DIBENZ(C,-F)IMIDAZO(1,5-A)AZEPINE-HYDROCHLORIDE

The invention relates to a process for preparing 3-amino-9,13b-dihydro-1H-dibenz[c,f]imidazo[1,5-a]azepine-hydrochloride.

This compound belongs to the group comprising the 2-aminoimidazolines and is a therapeutically effective substance which is particularly characterised by its antiallergic and antihistaminergic effect (U.S. Pat. No. 4,313,931).

Large numbers of 2-aminoimidazolines are known. In order to synthesise them, diamines are reacted with cyclising reagents such as O-alkylisoureas and S-alkylisothioureas, particularly N-acylated or N-carbalkoxylated O-alkylisoureas and S-alkylisothioureas. However, this method of synthesis involves numerous steps and requires laborious purifying procedures. It comprises the acylation or alkoxylation of the alkyliso(thio)ureas, condensation with the diamine, the cyclisation reaction and saponification of the acyl group.

Another disadvantage is the emission of equimolar quantities of alkylmercaptans which occurs when S-alkylisothioureas are used.

The cyclisation reaction using alkali metal cyanates leads to similar problems.

However, the cyclisation reaction to produce 2-aminoimidazolines with bromocyanogen occurs in a single reaction step.

A process of this kind for synthesising 3-amino-9,13b-dihydro-1H-dibenz[c,f]imidazo[1,5-a]azepine-hydrochloride is known from U.S. Pat. No. 4,313,931. The reaction steps are described as follows:

6-chloro-11H-dibenz[b,e]azepine is reacted with sodium cyanide, the resulting nitrile is reduced with lithium aluminium hydride and reacted with bromocyanogen to form the corresponding 2-aminoimidazoline base which is finally precipitated in the form of the hydrochloride from a methanolic suspension and then isolated. The yield is 41.8%.

However, within the scope of synthesis on an industrial scale, it is important not only to achieve high yields but also to obtain maximum possible throughput with the minimum technical expenditure.

This is not possible, however, with the process proposed in U.S. Pat. No. 4,313,931, because the reaction volumes cannot be increased without complex security measures, on account of the use of bromocyanogen, for example, which is a highly volatile, toxic substance. Moreover, each step of the reaction is followed by a purifying procedure, resulting in substantial losses of yield.

A further disadvantage is the reaction of the base to form the hydrochloride. The use of alcohols in the precipitation process as proposed in U.S. Pat. No. 4,313,931 results in a loss of quality caused by gradual decomposition of the product.

A procedure of this kind is complicated uneconomic and wasteful and is therefore not suitable for industrial production.

The aim of the present invention is to provide an industrial process which does not have the disadvantages of the prior art described above the makes it possible, in particular, to achieve a throughput of larger quantities of substance, whilst improving the quality of the end product.

It has now been found, surprisingly, that by hydrogenation of 6-phthalimidomethyl-5H-dibenz[b,e]-azepine (I), subsequent alkaline hydrazinolysis, reaction with bromocyanogen prepared in situ and precipitation of the resulting base (IV) in the form of the hydrochloride, the synthesis of 3-amino-9,13b-dihydro-1H-dibenz[c,-f]imidazo(1,5-a) azepine-hydrochloride (V) can be carried out so advantageously that industrial production is possible. Moreover, the process according to the invention involves a substantial increase in yield.

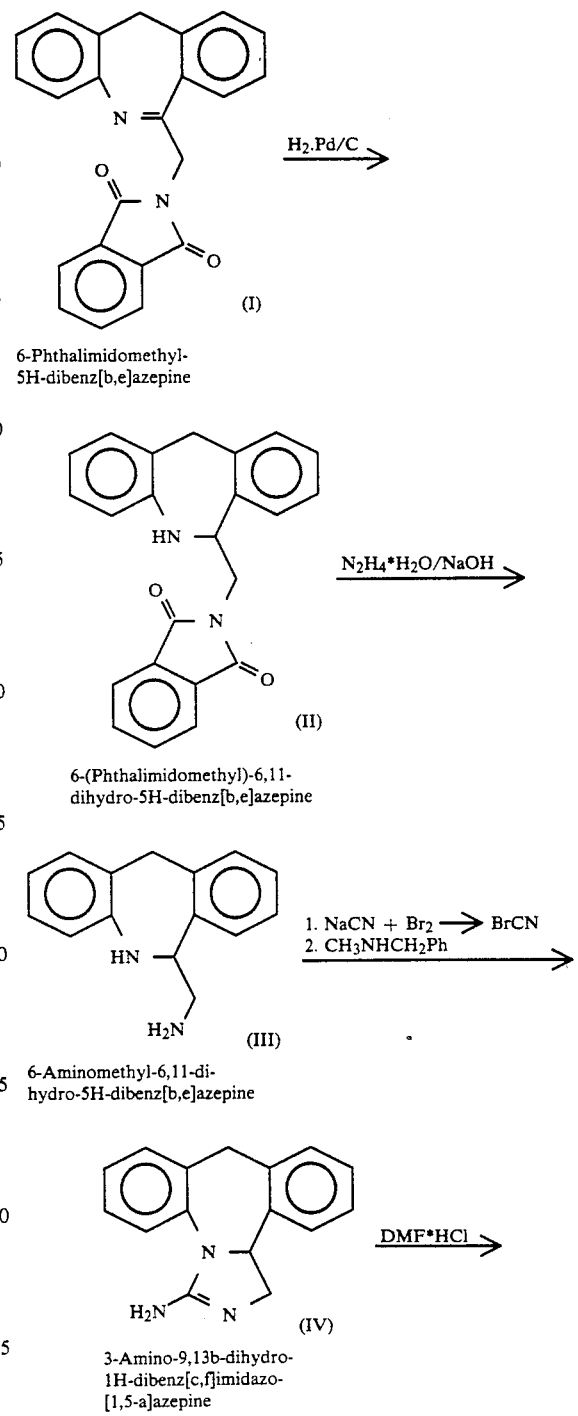

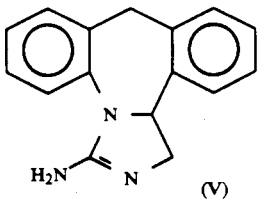

3-Amino-9,13b-dihydro-1H-
dibenz[c,f]imidazo[1,5-a]-
azepine-hydrochloride

For the hydrogenation, 6-phthalimidomethyl-5H-dibenz[b,e]azepine (I), which is obtainable by known methods, is reacted in dimethylformamide (if formic acid is used) or dimethylacetamide (if acetic acid is used) with hydrogen in a pressure range from 1 to 10 bar, preferably 6 to 8 bar, more particularly 7 bar, with palladium/charcoal catalyst, at a temperature of 40° to 100° C., preferably 60°–80° C., more especially 70° C. 0.5 to 5 mol/mol, preferably 1 to 3 mol/mol, and more especially 2 mol/mol of acetic or formic acid is added to the reaction mixture. If hydrogenation were carried out in pure organic acids, the reaction product would be precipitated and would then require laborious separation from the catalyst.

This effect advantageously permits a throughput of larger quantities of the substance. Moreover, the hydrogenation product need not be separated from the catalyst by additional extraction. After the reaction of hydrogenation, the catalyst can be filtered off and after some of the solvent has been distilled off, the product can be precipitated in a 90% yield by the addition of acetone.

In the process according to the invention, the hydrogenation product is subjected to an alkaline hydrazinolysis reaction, and the extracts from the reaction are reacted directly with bromocyanogen prepared in situ. For this purpose, 6-(phthalimido-methyl)-6,11-dihydro-5H-dibenz[b,e]azepine (II) is reacted with hydrazine hydrate in an alkaline mixture of water and a high-boiling liquid which is, however, immiscible with chlorohydrocarbons, e.g. ethyleneglycol, propyleneglycol, glycerol, preferably ethyleneglycol, for 2 hours at 100° to 150° C., preferably at 110°–120° C. An alkali metal hydroxide solution, preferably sodium hydroxide solution, is used as the base.

Alkaline hydrolysis after a hydrazinolysis reaction is known (Gibson, M. S. and Bradshaw, R. W., Angew. Chem. 80, 986–996 (1968)), but direct reaction with hydrazine in an alkaline solution, thus enabling direct extraction of the resulting amine (III), is not known.

In addition, the hydrazinolysis under alkaline conditions advantageously enables the quantity of hydrazine used to be reduced to stoichiometric amounts, thus making it considerably easier to handle this carcinogenic substance.

The process according to the invention, by using water-miscible, high boiling liquids such as glycol, makes it possible to increase the reaction temperature and thereby shorten the reaction times. In this way it is also possible to achieve direct extraction of the clean product with chlorohydrocarbons for the subsequent reaction with bromocyanogen. All impurities, e.g. the sodium salt of phthalic hydrazide which is produced during the reaction, remain in the aqueous phase, so that no separate purifying procedures are required. Extraction is carried out at 15° C. using a chlorinated hydrocarbon which is immiscible with the reaction mixture of the hydrazinolysis and which has a greater density; examples include chloroform, carbon tetrachloride, 1,2-dichloroethane, preferably dichloromethane.

For the reaction with bromocyanogen, the extraction phase is added to an aqueous solution formed from an aqueous sodium bromide solution which has been reacted with bromine at 5° to 25° C., preferably at 10° to 15° C., and then reacted with an aqueous sodium cyanide solution at 10° to 15° C. The bromocyanogen formed in situ thus reacts with the amine. Consequently, there is no direct handling of large quantities of bromocyanogen.

After the reaction has ended, a non-volatile base the reaction product of which with bromocyanogen is soluble in water or in benzene, toluene, xylene or halobenzene, is added in order to destroy the excess bromocyanogen. Examples of such bases include secondary monoamines such as N,N-dibenzylamine, N,N-dibutylamine, diethanolamine, diisopropylamine, as well as N-ethylbenzylamine, sarcosin-Na salt and preferably N-methylbenzylamine. After the base has been added, the mixture is refluxed for 15 minutes.

The handling of bromocyanogen on an industrial scale requires extensive safety procedures. Because the bromocyanogen in this case is produced in situ, it is possible to perform the reaction safely even on an industrial scale and at the same time to isolate the product in clean form without complex purification: for the selective precipitation of 3-amino-9,13b-dihydro-1H-dibenz[c,f]imidazo[1,5-a]azepine (IV) the organic solvent is distilled off, mixed with benzene or xylene or a halobenzene, but preferably with toluene, and the base is precipitated by the addition of sodium hydroxide solution. The resulting amine (IV) is obtained with a high degree of purity and in a yield of 76%.

The use of alcohols such as methanol as solvent for preparing the hydrochloride, as described in U.S. Pat. No. 4,313,931, leads to a gradual decomposition of the compound. Surprisingly, it has been found that 3-amino-9,13b-dihydro-1H-dibenz[c,f]imidazo[1,5-a]azepine can be precipitated from dimethylformamide in the form of the hydrochloride (V) in a virtually quantitative yield and with good stability.

To achieve this, the amine is dissolved, with heating, in dimethylformamide containing dissolved hydrochloric acid gas in a concentration ranging from 2.0 to 7.0 wt. -%, preferably 4.7 wt. -% and after filtration and partial distillation of the solvent the mixture is cooled. The hydrochloride is thus precipitated. After centrifuging, washing and drying, a yield of 90% is achieved.

The total yield of this process is 61.6%, compared with 41.8% for the process described in U.S. Pat. No. 4,313,931.

The process according to the invention thus represents a significant improvement over the processes of the prior art. This applies both to the throughput, which is increased in particular by the improved solubility of the hydrogenation product, and also to the reduction in the number of synthetic stages and purifying procedures required. Moreover, the reaction yield has been significantly improved.

The Examples which follow serve to illustrate the invention without restricting it.

EXAMPLE 1

Preparation of 6-(phthalimidomethyl)-6,11-dihydro-5H-dibenz[b,e]azepine (I)

A suspension of 110.0 kg of 6-phthalimidomethyl-5H-dibenz[b,e]azepine in 911.4 liters of dimethylformamide, 28.7 kg of formic acid and a suspension of 12.5 kg of 10% palladium charcoal in 25 liters of dimethylformamide is fed into a 1200 liter VA-propulsive jet loop reactor. The reaction mixture is heated to 70° C. and hydrogenated under 7 bar of absolute hydrogen pressure. After the catalyst has been filtered off and the reaction equipment and catalyst have been washed with 80 liters of dimethylformamide, 960 liters of dimethylformamide are distilled off from the combined filtrates at 70° to 80° C. After cooling to 50° C., 150 liters of acetone are added, then after further cooling to 15° C. the precipitated crystals are centrifuged off, washed with acetone and dried.

Yield: 99.5 kg of 6-(phthalimidomethyl)-6,11-dihydro-5H-dibenz[b,e]azepine (90% of theory)

EXAMPLE 2:

Preparation of 3-amino-9,13b-dihydro-1H-dibenz[c,f]imidazo[1,5-a]azepine (IV)

62.3 kg of 6-(phthalimidomethyl)-6,11-dihydro-5H-dibenz[b,e]azepine, 176 liters of glycol, 9 kg of hydrazine hydrate and 10.8 liters of 45% sodium hydroxide solution are introduced successively into a 1000 liter VA stirred apparatus and heated for 2 hours to 110° C. (solution 1).

Meanwhile, in a 500 liter enamel apparatus, 19.9 kg of anhydrous sodium bromide are dissolved in 88 liters of water and 29.6 kg of bromine are metered in at 10° to 15° C. Then, at 10° to 15° C., a mixture of 34.0 kg of 26.5% sodium cyanide solution and 35.2 liters of water are added (solution 2).

Solution 1 is cooled to 15° C., 315 liters of water are added and extraction is carried out with 140.8 liters of dichloromethane. The dichloromethane phase is mixed with solution 2 at 15° to 20° C. The extraction of solution 1 with 95 liters and 10 liters of dichloromethane is repeated twice and the extracts are also added to solution 2. The two-phase mixture is stirred overnight at 20° to 25° C., then 10.7 kg of N-methylbenzylamine are added and the mixture is refluxed for 15 minutes.

After the organic solvent has been distilled off, 88 liters of toluene and 39.6 liters of 45% sodium hydroxide solution are added at 60° C., then after 30 minutes the mixture is cooled to 5° C. and stirred for 30 minutes. The precipitate is centrifuged off, washed and dried.

Yield: 33.3 kg of 3-amino-9,13b-dihydro-1H-dibenz[c,f]-imidazo[1,5-a]azepine (76% of theory)

EXAMPLE 3

Preparation of 3-amino-9,13b-dihydro-1H-dibenz[c,f][1,5-a]azepine-hydrochloride (V)

In a 250 liter enamel apparatus, 60 kg of 6-(phthalimidomethyl)-6,11-dihydro-5H-dibenz[b,e]azepine, 157.9 liters of dimethylformamide and 48.4 kg of a 20% hydrochloric acid gas solution in dimethylformamide are introduced. After heating to 120° C. the solution is filtered and, after the apparatus has been washed with 23.6 liters of dimethylformamide, 75 to 80 liters of solvent are distilled off and the contents of the reaction apparatus are cooled to 5° C. The crystals obtained are removed by centrifuging, washed and dried.

Yield: 61.9 kg of 3-amino-9,13b-dihydro-1H-dibenz[c,f]-imidazo[1,5-a]azepine-hydrochloride (90% of theory)

What is claimed is:

1. A process for preparing 3-amino-9,13b-dihydro-1H-dibenz[c,f]imidazo[1,5-a]azepine-hydrochloride, which comprises:
   a) hydrogenating 6-phthalimidomethyl-5H-dibenz[b,e]-azepine i) in dimethylformamide and 0.5 to 5 mol/mol of formic acid, or ii) in dimethylacetamide and 0.5 to 5 mol/mol of acetic acid, in the presence of palladium/charcoal, at 1 to 10 bar of hydrogen pressure and at a temperature of 40° to 100° C., to produce 6-(phthalimidomethyl)-6,11-dihydro-5H-dibenz[b,e]azepine;
   b) reacting the 6-(phthalimidomethyl)-6,11-dihydro-5H-dibenz[b,e]azepine with hydrazine in an alkali metal hydroxide to produce 6-aminomethyl-6,11-dihydro-5H-dibenz[b,e]azepine;
   c) reacting the 6-aminomethyl-6,11-dihydro-5H-dibenz[b,e]azepine with bromocyanogen produced in situ to produce a reaction mixture;
   d) adding a base selected from the group consisting of N,N-dibenzylamine, N,N-dibutylamine, diethanolamine, diisopropylamine, N-ethylbenzylamine, sarcosin-Na salt and N-methylbenzylamine to the reaction mixture, to produce 3-amino-9,13b-dihydro-1H-dibenz[c,f]imidazo[1,5-a]azepine;
   e) dissolving the 3-amino-9,13b-dihydro-1H-dibenz[e,f]imidazo[1,5-a]azepine in a solvent selected from the group consisting of benzene, xylene, tolune and a halobenzene; and then adding a sodium hydroxide solution to effect precipitation;
   f) dissolving the precipitate produced in e) in dimethylformamide comprising from 2 to 7 wt.-% hydrochloric acid gas to produce a solution; and
   g) removing approximately one third of the dimethylformamide from the solution produced in f) by filtration and distillation, and then cooling the remainder of the solution to produce 3-amino-9,13b-dihydro-1H-dibenz[c,f]imidazo[1,5-a]azepine-hydrochloride.

2. The process as recited in claim 1 wherein the hydrogenation of 6-phthalimidomethyl-5H-dibenz[b,e]azepine is carried out in dimethylformamide and 2 mol/mol formic acid, or in dimethylacetamide and 2 mol/mol acetic acid, at 6 to 8 bar of hydrogen pressure and at a temperature of 60° to 80° C.

3. The process as recited in claim 1 wherein the reaction of 6-(phthalimidomethyl)-6,11-dihydro-5H-dibenz[b,e]azepine with hydrazine is carried out with hydrazine hydrate in an alkali metal hydroxide solution at between 100° to 150° C., in the presence of a higher-boiling water-miscible solvent which is immiscible with chlorohydrocarbons, and then extracted with a chlorinated hydrocarbon.

4. The process as recited in claim 1 wherein the reaction of 6-(phthalimidomethyl)-6,11-dihydro-5H-dibenz[b,e]azepine with hydrazine is carried out with hydrazine hydrate in a sodium hydroxide solution at between 110° to 120° C., in the presence of a higher-boiling water-miscible solvent selected from the group consisting of ethyleneglycol, propyleneglycol and glycerol, and then extracted with a chlorinated hydrocarbon selected from the group consisting of chloroform, carbon tetrachloride and 1,2-dichloroethane.

5. A process as recited in claim 1 wherein the reaction of 6-aminomethyl-6,11-dihydro-5H-dibenz[b,e]azepine with bromocyanogen is carried out as follows:
   a) reacting sodium bromide in an aqueous solution with bromine at 5° to 25° C., and then reacting the resultant solution with sodium cyanide at 10° to 15° C., to produce a bromocyanogen solution;
   b) adding the 6-aminomethyl-6,11-dihydro-5H-dibenz[b,e]azepine to the bromocyanogen solution and then stirring the resultant reaction mixture at 5° to 25° C.;
   c) adding a base selected from the group consisting of N,N-dibenzylamine, N,N-dibutylamine, diethanolamine, diisopropylamine, N-ethylbenzylamine, sarcosin-Na salt and N-methylbenzylamine to the reaction mixture to produce 3-amino-9,13b-dihydro-1H-dibenz[c,f]imidazo[1,5a]azepine; and
   d) dissolving the 3-amino-9,13b-dihydro-1H-dibenz[c,f]-imidazo[1,5-a]azepine in a solvent selected from the group consisting of benzene, xylene, toluene and a halobenzene, and then adding a sodium hydroxide solution to the resultant solution to effect precipitation.

6. A process as recited in claim 5 wherein the reaction of 6-aminomethyl-6,11-dihydro-5H-dibenz[b,e]azepine with bromocyanogen is carried out as follows:
   a) reacting sodium bromide in an aqueous solution with bromine at 10° to 15° C., and then reacting the resultant solution with sodium cyanide at 10° to 15° C., to produce a bromocyanogen solution;
   b) adding the 6-aminomethyl-6,11-dihydro-5H-dibenz]b,e]azepine to the bromocyanogen solution and stirring the resultant reaction mixture at 15° to 25° C.;
   c) adding a base selected from the group consisting of N,N-dibenzylamine, N,N-dibutylamine, diethanolamine, diisopropylamine, N-ethylbenzylamine, sarcosine-Na salt and N-methylbenzylamine to the reaction mixture to produce 3-amino-9,13b-dihydro-1H-dibenz[c,f]imidazo[1,5a]azepine; and
   d) dissolving the 3-amino-9,13b-dihydro-1H-dibenz[c,f]-imidazo[1,5-a]azepine in toluene and then adding a sodium hydroxide solution to the resultant solution to effect precipitation.

7. A process as recited in claim 1 wherein the precipitation of the 3-amino-9,13b-dihydro-1H-dibenz[c,f]imidazo]1,5-a]azepine is carried out as follows:
   a) dissolving the 3-amino-9,13b-dihydro-1H-dibenz[c,f imidazo[1,5-a]azepine, with heating, in dimethylformamide which comprises dissolved hydrochloric acid gas in a concentration range form 2.0 to 7.0 wt. -%, to produce a reaction mixture; and
   b) precipitating the 3-amino-9,13b-dihydro-1H-dibenz[c,f]imidazo[1,5-a]azepine-hydrochloride by removing about one third of dimethylformamide by filtration and distillation, and then cooling the resultant mixture.

* * * * *